United States Patent
Fan et al.

(10) Patent No.: US 10,390,796 B2
(45) Date of Patent: Aug. 27, 2019

(54) MOTION CORRECTION IN THREE-DIMENSIONAL ELASTICITY ULTRASOUND IMAGING

(71) Applicants: Liexiang Fan, Sammamish, WA (US); Art Schenck, Sammamish, WA (US)

(72) Inventors: Liexiang Fan, Sammamish, WA (US); Art Schenck, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 302 days.

(21) Appl. No.: 14/097,189

(22) Filed: Dec. 4, 2013

(65) Prior Publication Data

US 2015/0150535 A1     Jun. 4, 2015

(51) Int. Cl.
 *A61B 8/00* (2006.01)
 *A61B 8/08* (2006.01)
 *G01S 15/89* (2006.01)
 *G01S 7/52* (2006.01)

(52) U.S. Cl.
 CPC .............. *A61B 8/485* (2013.01); *A61B 8/085* (2013.01); *A61B 8/0875* (2013.01); *A61B 8/0891* (2013.01); *A61B 8/483* (2013.01); *A61B 8/5223* (2013.01); *A61B 8/5276* (2013.01); *G01S 7/52042* (2013.01); *G01S 7/52077* (2013.01); *G01S 15/8993* (2013.01); *G01S 7/52022* (2013.01)

(58) Field of Classification Search
 CPC combination set(s) only.
 See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,899,861 A * | 5/1999 | Friemel et al. | 600/443 |
| 6,508,768 B1 | 1/2003 | Hall et al. | |
| 6,558,324 B1 | 5/2003 | Von Behren et al. | |
| 2002/0040187 A1* | 4/2002 | Alam et al. | 600/442 |
| 2005/0187473 A1* | 8/2005 | Boctor | A61B 8/08 600/437 |
| 2006/0241443 A1* | 10/2006 | Whitmore et al. | 600/439 |
| 2007/0276236 A1* | 11/2007 | Jong | 600/437 |

(Continued)

FOREIGN PATENT DOCUMENTS

WO    WO 2012/080895    6/2012

OTHER PUBLICATIONS

L. S. Taylor et al., "Three dimensional sonoelastography: principles and practices," Phys. Med. Biol., vol. 45, No. 6, pp. 1477-1494, 2000.

(Continued)

*Primary Examiner* — Christopher L Cook

(57) ABSTRACT

Three-dimensional elasticity imaging is provided. Motion in three-dimensions due to sources other than the stress or compression for elasticity imaging is found from anatomical information. Objects less likely to be subject to the stress or compression and/or likely to be subject to undesired motion are used to find the undesired motion. This anatomical motion is accounted for in estimating the elasticity, such as removing the motion from echo data used to estimate elasticity or subtracting out the motion from motion generated as part of estimating elasticity.

15 Claims, 2 Drawing Sheets

(56) References Cited

U.S. PATENT DOCUMENTS

| | | | |
|---|---|---|---|
| 2008/0091678 A1* | 4/2008 | Walker et al. | 707/6 |
| 2012/0046521 A1* | 2/2012 | Hunter et al. | 600/104 |
| 2012/0065505 A1 | 3/2012 | Jeong et al. | |
| 2012/0203108 A1 | 8/2012 | Tsujita | |
| 2012/0283564 A1* | 11/2012 | Ebbini et al. | 600/439 |
| 2013/0028536 A1* | 1/2013 | Hazard | 382/275 |
| 2015/0366527 A1* | 12/2015 | Yu et al. | |

OTHER PUBLICATIONS

M. Muller et al., "Full 3D inversion of the viscoelasticity wave propagation problem for 3D ultrasound elastography in breast cancer diagnosis," Proc. IEEE Ultrasonics Symp., pp. 672-675, 2007.

M. Orescanin et al., "3-D FDTD Simulation of Shear Waves for Evaluation of Complex Modulus Imaging," IEEE Trans. UFFC, vol. 58, No. 2, pp. 389-398, 2011.

EP Search Report from counterpart EP application No. 14193643.5, dated May 29, 2015, 8 pages.

* cited by examiner

MOTION CORRECTION IN THREE-DIMENSIONAL ELASTICITY ULTRASOUND IMAGING

BACKGROUND

The present embodiments relate to elasticity imaging. In particular, the present embodiments relate to motion correction in elasticity imaging.

U.S. Pat. Nos. 5,107,837, 5,293,870, 5,178,147, and 6,508,768 describe methods to generate elasticity images using the relative tissue displacement between adjacent frames. Strain, strain rate, modulus, or other parameters corresponding to tissue displacement are detected for generating an elasticity image. U.S. Pat. No. 6,558,324 describes methods to represent elasticity using color coding. Other forms of elasticity imaging include shear and longitudinal wave imaging. Acoustic radiation force imaging also indicates the elasticity of tissue.

Elasticity imaging relies on differences in compression or tissue response over time to stress. Tissue deformation parameters, such as longitudinal and shear strain, or shear wave propagation parameters are secondary order estimates from phase or displacement information. Given a period over which data is collected, the elasticity imaging is susceptible to motion artifacts. It is a challenge to avoid displacement from sources other than the compression or stress for measuring elasticity. The patient may move, the transducer probe may move, and anatomy may move. The result is low quality, biased, low repeatability elasticity imaging.

For two-dimensional elasticity imaging, motion correction is applied to frames of echo data prior to elasticity estimation. The motion correction may remove some undesired distortions, but does not deal with out-of-plane motion.

BRIEF SUMMARY

By way of introduction, the preferred embodiments described below include methods, instructions and systems for elasticity ultrasound imaging. Three-dimensional elasticity imaging is provided. Motion in three-dimensions due to sources other than the stress or compression for elasticity imaging is found from anatomical information. Objects less likely to be subject to the stress for elasticity imaging and/or likely to be subject to undesired motion are used to find the undesired motion. This anatomical motion is accounted for in estimating the elasticity, such as removing the motion from echo data used to estimate elasticity or subtracting out the motion from motion generated as part of estimating elasticity.

In a first aspect, a method is provided for elasticity ultrasound imaging. An ultrasound system acquires first ultrasound data for a three-dimensional region. The first ultrasound data is voxels representing different locations distributed along three axes in the three-dimensional region at a first time. The ultrasound system acquires second ultrasound data for the three-dimensional region. The second ultrasound data is voxels representing the different locations distributed along the three axes in the three-dimensional region at a second time different from the first time. An anatomical landmark of the three-dimensional region and represented in the first and second ultrasound data is identified. Motion of the anatomical landmark from the first time to the second time is determined. Elasticity in the three-dimensional region is estimated from the first and second ultrasound data. In the estimating of elasticity in the three-dimensional region from the first and second ultrasound data, motion correcting as a function of the motion of the anatomical landmark is performed. A three-dimensional representation of the elasticity in the three-dimensional region is displayed.

In a second aspect, a non-transitory computer readable storage medium has stored therein data representing instructions executable by a programmed processor for elasticity ultrasound imaging. The storage medium includes instructions for acquiring echo data sequentially for a volume of tissue subjected to different stress at different times, tracking three-dimensional displacement of anatomy between the different times, calculating elasticities for the volume of the tissue from the echo data of the different times, accounting for the displacement of the anatomy in the elasticities, and generating an elasticity image from the elasticities.

In a third aspect, a method is provided for elasticity ultrasound imaging. An ultrasound system performs three-dimensional elasticity imaging with compression or acoustic radiation force. A processor removes motion other than caused by the compression or a wave resulting from the acoustic radiation force. The motion removed is a function of anatomic information representing structure less susceptible to the compression or the wave than soft tissue.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multiple volumes of echo data are acquired separately. The volumes represent a three-dimensional region of the patient while changing due to stress. The stress may be from an anatomical source, acoustic radiation force, or the transducer probe. Each voxel of the volumes is classified as an anatomical landmark or not an anatomical landmark. Landmark voxels are grouped, and the resulting anatomical information is tracked for motion to represent the undesired motion. The landmark motion is applied to the non-landmark voxels. In one approach, the landmark motion of the voxels is used to suppress motion caused by reverberation, scattering, or other undesired motion in the echo data, and elasticity for the different voxels is estimated from the motion corrected data. In another approach, motion for each of multiple voxels is estimated as part of elasticity calculation, and the anatomical motion is subtracted from the estimated motions for the voxels.

Figure 1:
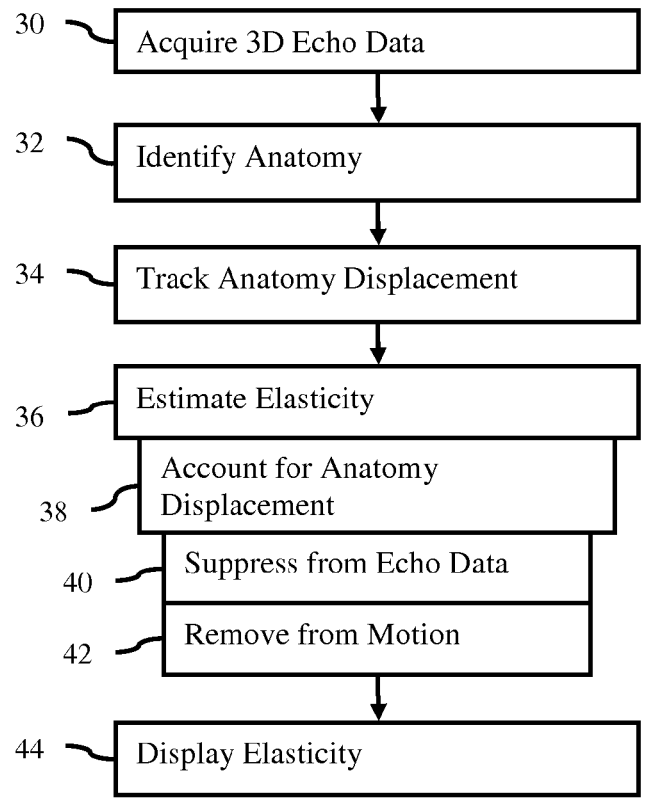
FIG. 1 is a flow chart diagram of one embodiment of a method for elasticity ultrasound imaging.

FIG. 1 shows a method for elasticity ultrasound imaging. In particular, three-dimensional elasticity imaging is performed by an ultrasound system. The response of tissue to compression, acoustic radiation force, or other source of stress is measured. A processor removes or reduces motion other than caused by the stress (e.g., caused by compression or a wave resulting from the acoustic radiation force). The motion being removed is based on anatomic information representing structure less susceptible to the stress. The result is elasticity estimation with less undesired motion. The motion used for elasticity imaging has fewer motion artifacts. Since the elasticity imaging is performed for three-dimensions, the motion is not susceptible to out-of-plane errors in motion estimation.

Additional, different or fewer acts may be provided in the method of FIG. 1. For example, one, both, or none of acts 40 and 42 are performed. As another example, the display act 44 is optional. The acts are performed in the order described or shown, but other orders may be provided.

In act 30, echo data is acquired sequentially for a volume of tissue subjected to different amounts of stress at different times. The echo data is acquired for a three-dimensional region. Frames or sets of data represent the same volume at different times. Any sampling of the volume may be used, such as a sector, Vector®, or linear sampling in three-dimensions. Scan lines responsive to a given transmission may be distributed in both azimuth and elevation. The scan pattern may sequentially cover scan lines distributed in azimuth and elevation. Alternatively, sequential scanning along planes separated in elevation is used to assemble data representing the volume.

The data is maintained in an acquisition format or converted (e.g., interpolated) to a regular three-dimensional grid. The data represents locations distributed along three axes, such as locations N×M×O where N, M, and O are integer numbers of locations along different axes and are each greater than one. The data for a location is a voxel. The volume of the patient is represented by frames or sets of voxels.

The acquired data represents the volume at different times. The scans to acquire the data are performed over different periods. Different amounts of stress are applied at the different periods. For example, the transducer probe is pressed against the patient by different amounts. As another example, a longitudinal or shear wave is generated with acoustic force radiation, a thumper, anatomy (e.g., heart or diaphragm), or other source. The wave passing through locations in the volume causes a variance in stress over time. Sets or frames of data are acquired over the periods or for times corresponding to the acquisition periods, but within a tissue response period. The tissue responds to the change in stress. The scanning is performed to acquire data representing the volume at different times while the tissue responds to the change. In alternative embodiments, the stress is repetitively applied, and frames are acquired at different amounts of time relative to the initiation of the stress.

In one embodiment, acoustic radiation force is used. An acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any acoustic radiation force impulse (ARFI) or shear wave imaging sequence may be used.

The transmission is configured by power, amplitude, timing, or other characteristic to cause stress on tissue sufficient to displace the tissue at one or more locations. For example, a transmit focus of the beam is positioned near a bottom, center of the field of view or region of interest (ROI) to cause displacement throughout the field of view. The transmission may be repeated for different sub-regions or ROIs.

The excitation is transmitted from an ultrasound transducer. The excitation is acoustic energy. The acoustic energy is focused, resulting in a three-dimensional beam profile. The excitation is focused using a phased array and/or mechanical focus. The excitation is transmitted into tissue of a patient.

The impulse excitation generates a longitudinal or shear wave at a spatial location. Where the excitation is sufficiently strong, a wave is generated. The shear wave propagates through tissue more slowly than the longitudinal wave propagates along the acoustic wave emission direction, so the type of wave may be distinguished by timing and/or direction. The difference in timing is used to isolate the shear wave from a longitudinal wave or vice versa. The wave propagates various directions, such as a direction perpendicular to the direction of the applied stress. The displacement of the wave is greater at locations closer to the focal location at which the wave is generated. As the wave travels, the magnitude of the wave attenuates.

In another embodiment, a user applies pressure axially while maintaining a transducer at a location. Ultrasound scanning is performed while applying different amounts of pressure with the transducer against the patient. In yet other embodiments, the stress caused by anatomy is used, such as heart motion.

Regardless of the form of stress, the echo data is acquired at different times to determine the displacement of the tissue in response to the change in stress. An ultrasound system scans the three-dimensional region of the patient while the region is subjected to the change in tissue deformation caused by the variance of stress (e.g., different pressures and/or wave).

The displacement is detected with ultrasound scanning. Ultrasound data is obtained. At least some of the ultrasound data is responsive to the wave or pressure. A region, such as a region of interest, entire field of view, or sub-region of interest, is scanned with ultrasound. For shear and longitudinal waves, the region is monitored to detect the wave. The echo data represents the tissue when subjected to different amounts of pressure at different times. The region is any size, such as 5×5 mm in lateral and 10 mm in axial. For example, B-mode scans are performed to detect tissue displacement. Doppler, color flow, or other ultrasound mode may be used to detect displacement.

For a given time, ultrasound is transmitted to the tissue or region of interest. Any now known or later developed displacement imaging may be used. For example, pulses with 1-5 cycle durations are used with an intensity of less than 720 mW/cm². Pulses with other intensities may be used. The scanning is performed for any number of scan lines. For example, eight or sixteen receive beams distributed in three-dimensions are formed in response to each transmission. After or while applying stress, B-mode transmissions are performed repetitively along a single transmit scan line and receptions along adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times.

The B-mode intensity may vary due to displacement of the tissue over time. For the monitored scan lines, a sequence of data is provided representing a time profile of tissue motion resulting from the stress. Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing the three-dimensional region at different times is received. The transmission and reception are performed multiple times to determine change due to displacement caused by the change in stress. By repetitively scanning with ultrasound, the position of tissue at different times is determined.

The acquired echo or ultrasound data is information used to estimate stiffness of tissue, such as strain. The data is responsive to compression force or other stress applied to the tissue being scanned.

In act 32, an anatomical landmark of the three-dimensional region is identified. The ultrasound data representing the volume of the patient at the different times represents at least one anatomical landmark. Any landmark may be used. For example, the volume includes soft tissue for which elasticity imaging is being performed. The soft tissue is part of an organ (e.g., liver tissue), muscle, skin, fat, breast, or other tissue with greater flexibility than bone and less fluid than blood or liquid. The anatomical landmark is a boundary (e.g., liver surface), bone, diaphragm, muscle, organ, vessel (e.g., vessel wall), or other structure of the patient. The anatomical landmark may be a tumor, cyst, or other structure in anatomy of the patient that is harder or stiffer than soft tissue, so less susceptible to the stress. The anatomical landmark may be tissue spaced from a region of interest so that less or greatly attenuated stress is applied to the tissue.

The anatomical landmark is chosen to be less susceptible to the stress. For example, the anatomy is stiffer and/or subject to a greater source of motion than the soft tissue being scanned for elasticity imaging. The anatomy is subject more to undesired motion than the motion caused by the stress. Any anatomy may be used, but anatomy with a greater response to undesired motion and/or lesser response to motion caused by the stress may be used to remove motion artifacts from the elasticity imaging. A specific landmark may be part of an anatomic structure or may be the anatomic structure itself. One or more anatomic structures may be used.

Any now known or later developed approach for detecting anatomy from ultrasound data may be used. For example, a processor applies edge detection, motion detection, region growing, thresholding, a machine-trained classifier, or image processing to locate specific anatomy. Filtering may be used, such as directional filtering applied to low pass filtered information to find a linear diaphragm.

The identification is performed automatically by a processor. In other embodiments, user assistance or use identification is provided. The user may confirm a processor identified anatomy, indicate a seed point for the anatomy, or trace the anatomy.

The anatomical landmark is represented by one or more voxels. For example, a bone or diaphragm is represented by a plurality of different voxels. The voxels are classified as representing the anatomy or not representing the anatomy. For example, all locations not identified as anatomy are treated as not representing the anatomy. As another example, a classifier outputs labels for each voxel as representing the anatomy or not.

Where more than one voxel is found to represent the anatomy, the voxels may be grouped. Different anatomy may be grouped separately or as a single group. The voxels classified as representing anatomy are grouped by labeling, segmenting, or other process.

In act 34, the anatomy is tracked between different times. The frames of echo data representing the volume at different times are used to track the anatomy. The motion of the anatomical landmark or group of anatomy voxels are tracked through a sequence of two or more sets of data. The displacement or change in position over time or between times is determined.

The tracking is in three-dimensions. A three-dimensional displacement vector is found. The vector is for a global motion. An average, overall, or other global indication of the motion for the volume is found. The grouped locations are used to find motion of the volume, such as motion caused by the patient, the transducer, reverberation, or scattering. The displacement is a translation and/or rotation in any number of degrees of freedom. The motion may be rigid or non-rigid (e.g., affine). The global motion may account for local distortions, such as twisting, compression, and/or stretching. In other embodiments, each voxel, separate anatomy, or other separate tracking is performed for different anatomy.

Any now known or later developed tracking may be used. In one embodiment, the anatomy is identified in each set of data. The displacement of the anatomy between sets is determined by any translation and/or rotation between sets. In other embodiments, the anatomy is identified in one frame. The identified voxels are correlated with all the voxels of another frame to find the displacement. Any correlation or other similarity measure (e.g., sum of absolute differences) are used. Different possible displacements are tested and the one with the greatest similarity is selected.

The tracking provides a transform or displacement field. The displacement for each voxel of the identified anatomy (e.g., grouped anatomy voxels) is represented in the field or transform. For rigid motion, the same displacement is provided for each voxel. For non-rigid motion, different voxels have different three-dimensional displacement. A three-dimensional displacement vector is provided for each of the voxels of the anatomical landmark or landmarks.

In act 36, the elasticity is estimated. An elasticity value is calculated for each of different locations in the volume. Elasticities are calculated for all the voxels or just a sub-set of the voxels. For example, elasticity is calculated for each of the voxels not classified as an anatomical landmark or just voxels in a region of interest. The elasticity of tissue in the volume is estimated.

Elasticity or elastography are general terms that include various types of parametric images of tissue stiffness, such as strain, strain rate, modulus or relaxation, and various methods of mechanically generating them. Strain images show tissue relative stiffness and deformation. Strain rate images display the first time derivative of the strain. Local strain rate may indicate cardiac muscle contractility from which is inferred the muscle health and condition. Modulus images (e.g., Young's modulus) may be generated when the strain image or strain rate image is normalized by and combined with stress measurements. One method is to measure the pressure at the body surface with sensors attached to the transducer. The stress field pattern is then extrapolated internally to the points (i.e., pixels or voxels) of measured strain. Young's modulus is defined as stress divided by strain. Local modulus values may be calculated and those numerical values are converted to gray scale or color values for display. In strain (e.g., shear) imaging, local three-dimensional displacements are measured and the numerical displacement, velocity or other values are converted to gray scale or color values for display. The direction of strain may be mapped to color or other display characteristic.

Strain images may be generated with manual palpation, external vibration sources, inherent tissues motion (e.g., motion due to cardiac pulsations, or breathing) or acoustic radiation force imaging (ARFI). ARFI produces strain images or produces relaxation images. Relaxation images may be displayed parametrically in similar fashion to strain and modulus images. The parametric images are generated with four (e.g., dynamic volumetric) dimensional acquisition and imaging. In one embodiment, any one or more of the methods or systems disclosed in U.S. Pat. Nos. 5,107,837, 5,293,870, 5,178,147, 6,508,768 or 6,558,324, the disclosures of which are incorporated herein by reference, are used to generate elasticity frames of data or images with a three-dimensional scan pattern (e.g., scan lines spaced apart in azimuth and elevation). Any now know or later developed elasticity estimation may be used.

In one embodiment, the elasticity is estimated from the displacement over time of the tissue. The displacement is detected for each of multiple spatial locations. For example, the velocity, variance, shift in intensity pattern (e.g., speckle tracking), or other information is detected from the received data as the displacement between two times. An ongoing or sequence of displacements may be detected for each of the locations.

In one embodiment using B-mode data, the data from different scans is correlated as a function of time. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations and/or rotations between the two data sets are performed.

The reference is a first or other set of data or data from another scan. The reference set is from before the stress, but may be from after the stress. The same reference is used for the entire displacement detection, or the reference data changes in an ongoing or moving window.

The correlation is three-dimensional. The translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

Figure 2:
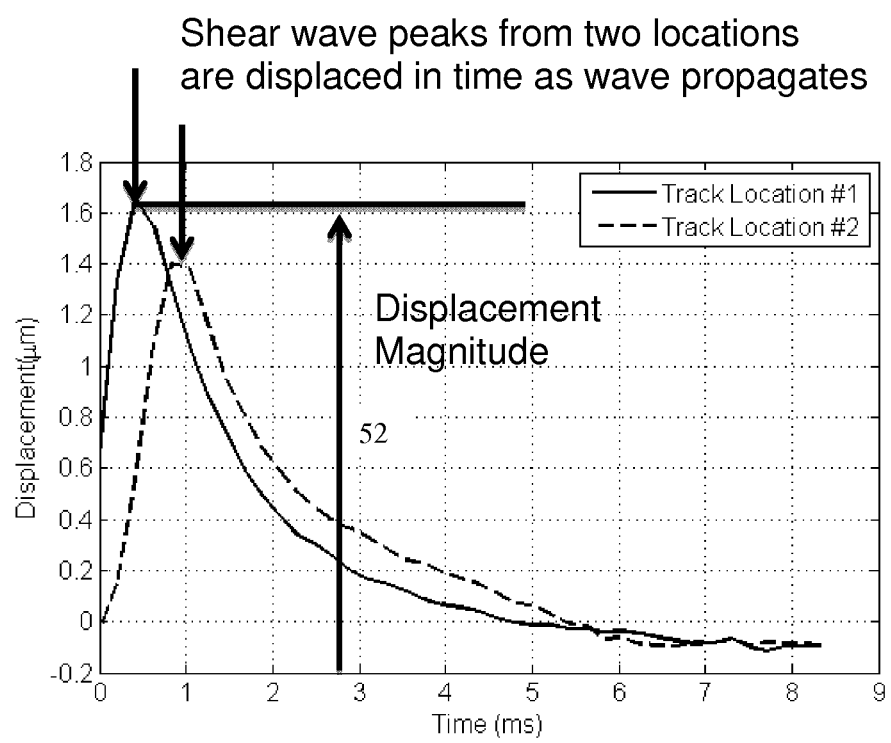
FIG. 2 is a graph showing two example displacement profiles as a function of time.

FIG. 2 shows two example displacement profiles of displacements for a voxel. The amplitude in distance of the motion vector over time from the reference data is shown. The period of analysis is over about 8 milliseconds, but may be longer or shorter (e.g., 12 milliseconds at a 4.8 kHz sample rate). Other displacement profiles are possible. Any number of locations may be measured for displacement, such as measuring every millimeter in the 10×5 mm region of interest. Displacement for each location and for each sample time is measured. This displacement data represents a profile of amplitude as a function of time for a location. Similar profiles are calculated for other locations.

The displacements over time and/or space are used for calculation. In one embodiment, the displacements for different depths are combined, leaving displacements spaced in azimuth and elevation. For example, the displacements for a given scan line or lateral location are averaged over depth. Alternatively to averaging, a maximum or other selection criterion is used to determine the displacement for a given lateral location. Displacements for only one depth may be used. Displacements for different depths may be used independently.

Elasticity is estimated from the displacement profile. In one embodiment, the peak or maximum amplitude in the profile is determined. Based on a distance of the voxel from the source of the stress for wave-based elasticity, a difference in time between application of the stress and the peak amplitude indicates a velocity. A difference in velocity between locations is used as elasticity. In an alternative approach, the displacement profiles from different locations are correlated to find a delay between the locations. This phase shift may be used to calculate the velocity between the locations associated with the correlated profiles.

In embodiments using an external or non-focused source of pressure, a displacement between a frame associated with stress and one without is calculated. The displacement without a temporal profile may be used as the elasticity. Multiple displacements for a given location due to different levels of stress may be averaged or combined.

In other embodiments, analytic data is calculated from the displacement profile and phase shift is used to determine the elasticity. A difference in phase over time of the displacements of different voxels or a zero-crossing of the phase for a given voxel indicates a velocity. The velocity may be used as the or to estimate the elasticity.

In act 38, the displacement of the anatomy is accounted for in the estimation of the elasticities in act 36. The elasticity values are a function of the correction for undesired motion. The undesired motion is indicated by the displacement or motion of the anatomy. The motion field, motion value, transform, or other indicator of motion of the anatomic landmark is used in the estimation of the values for elasticity to reduce motion artifacts or other distortion caused by undesired motion (i.e., motion other than caused by the stress for elasticity imaging).

The anatomic motion is based on voxels representing anatomy. The elasticity values are estimated for those same voxels, other voxels (non-anatomical landmark soft tissue), or both. For the anatomy voxels, the three-dimensional motion vector of the anatomy is known from act 34. For other voxels, the anatomic motion is used. For a single global motion, the global motion is applied to all of the voxels. Where a field or transform of different motions (e.g., non-rigid) is provided for the voxels representing anatomy, the anatomy motion is interpolated, extrapolated, modeled, or otherwise determined from the anatomy motion of the anatomy voxels for the other voxels. For example, the motion field is fit to a model for the relevant volume of the patient, and the model provides motion for the other, soft tissue voxels. The model fitting may be used to determine motion for other times as well as other locations. As another example, a nearest neighbor or extrapolation from the nearest four, six, or other number of neighboring anatomy voxels is used. The undesired motion represented by anatomic motion is expanded to the voxels not representing the anatomical landmark used to determine the undesired motion. Since the motion is a three-dimensional vector with or without rotational components, a three-dimensional expansion (e.g., interpolation) is used.

Acts 40 and 42 indicate two approaches for accounting for the anatomy displacement. One or both approaches may be used. For example, part of the undesired motion (e.g., some but not all dimensions and/or part of but not all of the amplitude of the motions) is corrected in one approach and the remaining in the other. In other embodiments, a different approach or approaches are used.

In act 40, the displacement caused by the anatomy motion is suppressed in the ultrasound or echo data prior to calculating the elasticity values and prior to calculating displacements. Prior to determining the displacement caused by the change in stress over time, the anatomy motion is suppressed. One set of ultrasound data is motion corrected relative to another set for the voxels. The undesired aspect of the motion, as indicated by the motion based on the anatomic landmark, is removed from the echo data prior to calculating the displacement of tissue for each voxel for elasticity imaging. Voxels are offset to account for the undesired motion so that the locations represented by the voxels are aligned other than motion caused by the stress. For example, reverberation or scattering effects are included in the motion tracking of the anatomy, so correction for anatomical motion removes some of the effects of reverberation or scattering.

Any motion correction may be used. The echo data may be filtered with a spatial translation and/or rotation operation. The inverse of the anatomy motion or motion field is applied to adjust a later set of data to an earlier set of data. Conversely, the motion is added to the earlier set of data to adjust to the later set. Interpolation or nearest neighbor approaches may be used to determine echo data values in a regular grid after motion correction. The displacements and elasticity are calculated from the motion corrected echo data.

In act 42, the motion correction is a subtraction of motion from motion estimated for the elasticity imaging. For example, the displacement of a voxel over time is calculated (see FIG. 2). The motion of a given voxel for elasticity estimation is determined as a total motion. This displacement over time is represented by a sequence of three-dimensional vectors. Similarly, a sequence of three-dimensional vectors representing the motion of the anatomy over time or motion derived from the anatomy motion (e.g., for non-anatomy voxels) is provided for the voxel. By subtracting the anatomy-based motion from the calculated displacements for elasticity imaging, the undesired motion information is removed from the displacements. A three-dimensional vector subtraction is performed. Operations other than subtraction may be used to remove the undesired motion from the motion estimated for elasticity imaging. The elasticity is then estimated from the corrected displacements.

In act 44, an elasticity image is generated. After accounting for the undesired motion, as reflected by the displacement of the anatomy, elasticity values for different voxels are estimated in act 36. These elasticities are mapped to image values for displaying an elasticity image. Any now known or later developed elasticity imaging may be used. For example, a shear wave, longitudinal wave, strain, or other image is generated. One image or a sequence of images is generated.

Since the elasticities represent voxels or different locations in a volume, two or three-dimensional imaging may be used. For two-dimensional imaging, elasticity values along a user or processor defined plane are extracted and used to generate the image. Multi-planar reconstruction may be used. For three-dimensional imaging, any rendering technique may be used, such as maximum intensity projection. Alpha blending or other approaches may be used. The volume is rendered to a two-dimensional display. A three-dimensional representation of the elasticity in the three-dimensional region is generated. Animation may be added by shifting the perspective for the rendering, allowing the user to view the volume from different directions. The more opaquely rendered stiff regions may be better appreciated by animation of the view.

The elasticity image is displayed alone. Alternatively, a B-mode or other image representing the same region or a different field of view is displayed adjacent to the elasticity image. In another alternative embodiment, the elasticity image is combined with or overlaid on the B-mode image.

Figure 3:
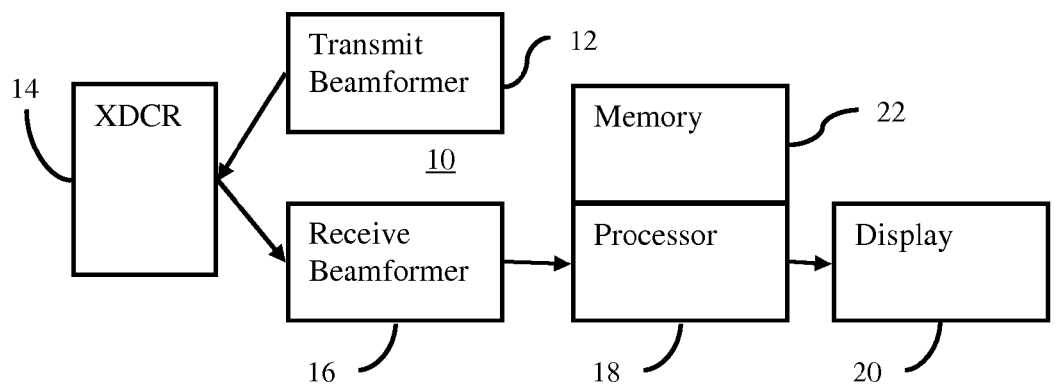
FIG. 3 is a block diagram of one embodiment of a system for elasticity ultrasound imaging.

FIG. 3 shows one embodiment of a system 10 for three-dimensional elasticity ultrasound imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. The system 10 is configured to acquire echo data distributed over three-dimensions for elasticity imaging of a volume (e.g., act 30 of FIG. 1). In alternative embodiments, the system 10 is a personal computer, workstation, PACS station, or other arrangement at a same location or distributed over a network for real-time or post acquisition imaging. The system 10 acquires data from a memory or another ultrasound imaging system.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a three-dimensional region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear or longitudinal wave imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 may generate impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force impulse pulses. In other embodiments, a probe housing or other device is used to apply stress to the tissue of the patient.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event may provide a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient undergoing a change in stress.

The transducer 14 is a 1-, 1.25-, 1.5-, 1.75-or 2-dimensional array of piezoelectric or capacitive membrane elements. A wobbler array may be used. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing a three-dimensional region at different times. After the acoustic impulse excitation, the receive beamformer 16 generates beams representing locations along a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for locations for a volume (e.g., voxels) are output. Dynamic focusing may be provided. The data may be for different purposes. For example, different scans are performed for B-mode or tissue data than for elasticity. Alternatively, the B-mode data is also used to determine elasticity. As another example, data for shear imaging are acquired with a series of shared scans, and B-mode or Doppler scanning is performed separately or using some of the same data. The ultrasound or echo data is from any stage of processing, such as beamformed data before detection or data after detection.

The processor 18 is a B-mode detector, Doppler detector, pulsed wave Doppler detector, correlation processor, Fourier transform processor, application specific integrated circuit, general processor, control processor, image processor, field programmable gate array, graphics processing unit, digital signal processor, analog circuit, digital circuit, combinations thereof or other now known or later developed device for detecting and processing information for display from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, graphics processing unit, data path, combinations thereof or other now known or later developed device for anatomy identification, anatomy motion tracking, elasticity estimation, and accounting for undesired motion in the elasticity estimation. Attenuation, shear modulus, shear viscosity, or one or more other properties of shear wave propagation may be estimated. The processor 18 generates a three-dimensional representation as an elasticity image. For example, the separate processor is configured by hardware and/or software to perform any combination of one or more of the acts 32-44 shown in FIG. 1.

The processor 18 is configured to estimate tissue displacement induced by the acoustic impulse excitation or other stress. Using correlation, tracking, motion detection, or other displacement measuring, the amount of shift in position of the tissue is estimated. The estimation is performed multiple times through a period, such as from prior to the tissue moving due to stress to during stress or after the tissue has mostly or completely returned to a relaxed state (e.g., recovered from the stress caused by the impulse excitation). Alternatively, a single shift is estimated. Differences in shift of the tissue between locations indicate relative stiffness or elasticity.

The processor 18 is configured to identify anatomy or one or more locations of an anatomical landmark. For example, anatomy spaced from a region of application of stress is identified. Due to the spacing, the anatomy may be less susceptible to motion or change caused by the stress but still susceptible to other causes of motion or change. The processor 18 is configured to track the motion of the anatomy, such as a tissue boundary, different organ than being examined for elasticity, vessel, diaphragm, bone, tissue directly attached to bone, or fluid filled chamber. The change in position of the anatomy is used to represent undesired sources of change in elastography.

The processor 18 is configured to estimate elasticity values. Phase change detection, correlation, displacement determination, peak identification, velocity calculation, stress measures, stress attenuation, and/or other processes may be used to estimate elasticity. The processor 18 is configured to account for the undesired motion in the estimation. The motion of the anatomy is removed, suppressed, or corrected in the echo data prior to estimating displacements and elasticity values with the echo data. Alternatively or additionally, total motion or change is determined as part of estimating elasticity values. The undesired motion is then subtracted from the motion, resulting in motion more likely due to the stress.

The processor 18 is configured to generate one or more images. For example, a shear wave velocity image is generated. Other elastography images may be generated, such as a shear modulus, strain, or strain rate image. The elastography image is presented as an overlay or region of interest within a B-mode image. The elasticity values modulate the color at locations in the region of interest. Where the elasticity value is below a threshold, B-mode information may be displayed without modulation by the elasticity value.

The image is a three-dimensional rendering or a planar reconstruction. The distribution of elasticity values in a volume is used to render to a display. A three-dimensional representation shows the elasticity values. For example, a rotating perspective display is shown. Using maximum intensity projection, regions or locations associated with stiffer soft tissue are displayed more opaquely. Bone or other tissue above a level of stiffness may be masked.

The processor 18 operates pursuant to instructions stored in the memory 22 or another memory for three-dimensional elasticity ultrasound imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The two dimensional images represent spatial distribution in an area, such as a plane reconstructed from data representing a volume. The three-dimensional representations are rendered from the data representing spatial distribution in a volume. The display 20 is configured by the processor 18 or other device by input of the signals to be displayed as an image. The display 20 displays an image representing elasticity for different locations in a region of interest.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for elasticity ultrasound imaging, the method comprising:

acquiring, with an ultrasound system, first ultrasound data for a three-dimensional region, the first ultrasound data comprising voxels representing different locations distributed along three axes in the three-dimensional region at a first time;

acquiring, with the ultrasound system, second ultrasound data for the three-dimensional region, the second ultrasound data comprising voxels representing the different locations distributed along the three axes in the three-dimensional region at a second time different than the first time and while a region of interest for elasticity estimation is subject to application of stress, the region of interest being within the three-dimensional region;

identifying an anatomical landmark of the three-dimensional region and spaced from the region of interest for elasticity estimation and from a region of application of the stress, the anatomical landmark represented in the first and second ultrasound data, the identifying being by detection of a structure as the anatomical landmark by a processor processing each of the first ultrasound data for the structure and the second ultrasound data for the structure; then determining motion of the anatomical landmark based on a difference in position as identified from the first time to the second time;

estimating elasticity in the three-dimensional region from the first and second ultrasound data, the elasticity estimated in the region of interest in the three-dimensional region;

motion correcting in the estimating of elasticity in the three-dimensional region from the first and second ultrasound data, the motion correcting being a function of the motion of the anatomical landmark; and displaying a three-dimensional representation of the elasticity in the three-dimensional region.

2. The method of claim 1 wherein acquiring the first and second ultrasound data comprises scanning the three-dimensional region while the three- dimensional region is subjected to a change in tissue deformation.

3. The method of claim 2 wherein scanning comprises scanning while the three-dimensional region is subjected to a longitudinal or shear wave as the stress, wherein estimating comprises estimating tissue response to the longitudinal or shear wave, and wherein displaying comprises generating the three- dimensional representation as a longitudinal or shear wave image.

4. The method of claim 2 wherein scanning comprises scanning while the three-dimensional region is subjected to different pressures as the stress, wherein estimating comprises estimating the tissue response to the different pressures, and wherein displaying comprises generating the three-dimensional representation as a strain image.

5. The method of claim 1 wherein acquiring the first and second ultrasound data comprise acquiring with the first and second times being within a tissue response period to the applied stress.

6. The method of claim 1 wherein identifying the anatomical landmark comprises identifying by the processing of the first and second ultrasound data that the voxels represent a vessel, a diaphragm, bone, tumor, or cyst.

7. The method of claim 1 wherein identifying the anatomical landmark comprises identifying by the processing of the first and second ultrasound data that voxels represent the anatomical landmark and grouping the voxels identified as representing the anatomical landmark.

8. The method of claim 1 wherein determining the motion comprises motion tracking the anatomical landmark, the motion being a three-dimensional displacement vector for each voxel of the anatomical landmark.

9. The method of claim 1 wherein determining the motion comprises determining a rigid or non-rigid transform of the anatomical landmark between the first and second times.

10. The method of claim 1 wherein estimating comprises determining a phase change between the first and second ultrasound data for each of the voxels.

11. The method of claim 1 wherein estimating comprises determining a displacement between the first and second times of soft tissue in the three-dimensional region for each of a plurality of voxels.

12. The method of claim 1 wherein motion correcting comprises motion correcting the second ultrasound data relative to the first ultrasound data for voxels not representing the anatomical landmark and representing soft tissue prior to estimating the elasticity from the first and second ultrasound data.

13. The method of claim 1 wherein estimating comprises estimating displacement motion between the first and second times for each of a plurality of the voxels, and wherein motion correcting comprises removing the motion of the anatomical landmark from the displacement motion.

14. The method of claim 1 wherein motion correcting comprises motion correcting the voxels for tissue different than the anatomical landmark based on a model of motion from the motion of the anatomical landmark.

15. The method of claim 1 wherein identifying comprises identifying the anatomical landmark as being less susceptible to the stress used for estimating the elasticity than tissue for which the elasticity is estimated.

* * * * *